(12) United States Patent
Riegels et al.

(10) Patent No.: US 7,183,086 B2
(45) Date of Patent: *Feb. 27, 2007

(54) ENZYMATIC HYDROLYSIS OF CYCLIC OLIGOMERS

(75) Inventors: Martin Riegels, Leichlingen (DE); Rainhard Koch, Cologne (DE); Lars Saaby Pedersen, Farum (DK); Henrik Lund, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 286 days.

This patent is subject to a terminal disclaimer.

(21) Appl. No.: 10/373,510

(22) Filed: Feb. 25, 2003

(65) Prior Publication Data

US 2004/0009564 A1    Jan. 15, 2004

Related U.S. Application Data

(63) Continuation of application No. 09/677,232, filed on Oct. 2, 2000, now Pat. No. 6,548,278, which is a continuation of application No. 09/119,892, filed on Jul. 21, 1998, now Pat. No. 6,184,010, which is a continuation of application No. PCT/DK97/00025, filed on Jan. 20, 1997.

(30) Foreign Application Priority Data

Jan. 22, 1996  (DK) .................................... 0066/96

(51) Int. Cl.
   *C12P 7/62* (2006.01)
(52) U.S. Cl. .................. 435/135; 435/134; 435/196; 435/136; 435/145
(58) Field of Classification Search .................. None
   See application file for complete search history.

(56) References Cited

U.S. PATENT DOCUMENTS 4,362,852 A    12/1982    Pendlebury et al.
5,273,897 A    12/1993    Sato et al.

FOREIGN PATENT DOCUMENTS

JP           56118420         9/1981

OTHER PUBLICATIONS

Foster, et al., FEMS Microbiology Letters, vol. 118, pp. 279-282 (1994).*
Kollattukudy, (1984) Borgstrom et al. (editors) Elsevier 472-504.
Longhi et al. (1999) Biochimica et Biophysica Acta 1441:185-196.
Carvalho et al. (1999) Biot. & Bioeng. 66(1):17-34.
Tokiwa et al., Agric. Biol. Chem., vol. 50, pp. 1323-1325 (1986).
Smith et al., Journal of Biomedical Matreials Research, vol. 21, pp. 991-1003 (1987).
Sato, Sen-I Gakkaishi, vol. 39, No. 5, pp. 67-77 (1983).
McIntyre, Polyester Fibres, vol. IV, pp. 1-71 (1985).
Wiley et al., Encyclopedia of Chem. Tech., 4th ed., vol. 10 (1993).
Academic Press Inc., Enzyme Nomenclature, pp. 305-315 (1992).
Cimecioglu et al., J. Applied Polymer Sci., vol. 32, pp. 4719-4733 (1986).
Wick et al., Die Angewandte Makromoleculare Chemie, vol. 112, No. 1771, pp. 59-94 (1983).
Derminot et al., Bull. Sci. Inst. Textile France, vol. 19, pp. 215-229 (1976).
Derminot et al., Industrie Textile, vol. 1083, pp. 677-681 (1978).
Lin et al., Physiol Plant Path., vol. 17, pp. 1-15 (1980).
Kolattukudy, Science, vol. 208, pp. 990-1000 (1980).
Sato, Sen-I Gakkaishi, vol. 37, pp. 80-90 (1981).
Cimecioglu et al., Journal of Applied Polymer Science (1986) 32:4719-4733.
STN International, File CAPLUS, CAPLUS Accession No. 1982:7275, Teijin Ltd: JP A2 56118420, 810917, Showa.
Fukumura et al., "Hydrolysis of Cyclic and Linear Oligomers of 6-Aminocaproic Acid by a Bacterial Cell Extract", The Journal of Biochemistry, vol. 59, No. 6 (1966).
Fukumura et al., "Loss of ε-Aminocaproate Metabolism in *Corynebacterium aurantiacum*" J. Ferment. Technol., vol. 60, No. 5, p. 469-472 (1982).
Kakado et al., "Characterization of Endo-Type 6-Aminohexanoate-Oligomer Hydrolase From *Flavobacterium* sp.", Journal of Fermentation and Bioengineering, vol. 80, No. 1, pp. 12-17 (1995).

* cited by examiner

*Primary Examiner*—Irene Marx
(74) *Attorney, Agent, or Firm*—Elias Lambiris

(57) ABSTRACT

The present invention relates to a process for enzymatic hydrolysis of cyclic oligomers of poly(ethylene terephthalate), which process comprises subjecting the cyclic oligomer to the action of one or more lipolytic and/or biopolyester hydrolytic enzyme(s).

18 Claims, No Drawings

ENZYMATIC HYDROLYSIS OF CYCLIC OLIGOMERS

CROSS-REFERENCE TO RELATED APPLICATIONS

This application is a continuation of U.S. patent application Ser. No. 09/677,232, filed on Oct. 2, 2000, now U.S. Pat. No. 6,548,278, which is a continuation of U.S. patent application Ser. No. 09/119,892, filed on Jul. 21, 1998, (now a U.S. Pat. No. 6,184,010), which is a continuation of PCT/DK97/00025 filed on Jan. 20, 1997, which claims priority under 35 U.S.C. 119 of Danish application no. 0066/96, filed on Jan. 22, 1996, the contents of which are fully incorporated herein by reference.

TECHNICAL FIELD

The present invention relates to a process for enzymatic hydrolysis of cyclic oligomers of poly(ethylene terephthalate), which process comprises subjecting the cyclic oligomer to the action of one or more carboxylic ester hydrolases.

BACKGROUND ART

Poly(ethylene terephthalate) fibers accounts for the main part of the polyester applied by the textile industry. The fibers are produced by e.g. poly-condensation of terephthalic acid and ethylene glycol, and drawing of fibers from a melt. During these processes, at high temperatures, cyclic oligomers, in particular cyclic tri(ethylene terephthalate), are formed in and on the fibers. Cyclic oligomers tend to give fabrics with a content of poly(ethylene terephthalate) fibers a grayish appearance. This is due to deposits of cyclic oligomers on the surface of the fabric, which is particularly outspoken after high temperature wet processes like HT (high temperature) dyeing. The cyclic oligomers are difficult to remove and may even be resistant to an alkaline post treatment [cf. G. Valk et al.; Melliand Textilberichte 1970 5 504–508]. Therefore, to be effective, the alkaline treatment has to be severe, which results in a significant loss of fiber material. Also, organic extraction of the cyclic oligomers is a technical possibility, but not industrially feasible.

SUMMARY OF THE INVENTION

It is an object of the present invention to provide an enzymatic process for removal of cyclic oligomers of poly (ethylene terephthalate), in particular cyclic tri(ethylene terephthalate), by which process the cyclic oligomers are enzymatically hydrolyzed to linear fragments, which can then be removed under gentle conditions, or which may even be leftover. Thus the process of the invention avoids the need for harsh chemicals or organic extraction.

Accordingly, the invention provides a process for enzymatic hydrolysis of cyclic oligomers of poly(ethylene terephthalate), which process comprises subjecting the cyclic oligomer to the action of one or more carboxylic ester hydrolases.

DETAILED DISCLOSURE OF THE INVENTION

The present invention relates to a process for enzymatic hydrolysis of cyclic oligomers of poly(ethylene terephthalate). More specifically the invention provides a process for enzymatic hydrolysis of cyclic oligomers of poly(ethylene terephthalate), which process comprises subjecting the cyclic oligomer to the action of one or more carboxylic ester hydrolases, in particular lipolytic and/or biopolyester hydrolytic enzyme(s). In the context of this invention a biopolyester is a polyester of biological origin.

The process of the invention may in particular be applied to yarns or fabrics with a content of poly(ethylene terephthalate) fibers, during which process the content of cyclic oligomers, which were formed as byproducts during synthesis and processing of the fibers, becomes eliminated or at least significantly reduced.

Polyester Fabrics

Poly(ethylene terephthalate) is synthesized by condensation, drawn into fibers from a melt, possibly cut to stables, possibly mixed with other fiber types, and spun to yarn. The yarn is dyed and knitted into cloth or made into carpets, or the yarn is woven into fabric and dyed. These processes can be followed by finishing (post treatment) steps.

During synthesis and drawing, cyclic oligomers of poly (ethylene terephthalate) are formed on and in the fibers. These cyclic oligomers are partly deposited on machinery, partly staying on/in the fibers, which turns out to give an undesirable grayish appearance of the final fabric or carpet.

Cyclic oligomers can be removed by organic extraction, but such a process is not industrially feasible due to cost and problems in handling and regeneration of large quantities of organic solvents. Cyclic oligomers can also be removed by an alkaline post scouring step, but to be effective the alkaline treatment has to be severe and results in significant loss of fiber material, too.

According to the present invention, removal of cyclic oligomers, in particular cyclic trimers, can be accomplished by hydrolysis with one or more hydrolytic enzymes. The enzyme breaks the ring structure of the cyclic oligomer by hydrolyzing an ester bond. The resulting product creates less of a problem, because it can be removed under gentle conditions or even leftover in the product.

The enzymatic treatment does not have the disadvantages valid for organic extraction and alkaline post scouring, in particular is does not require large quantities of organic solvent to be involved, and there is no significant loss of fiber material.

The process of the invention is readily applicable in the textile industry as it can be carried out using existing wet processing apparatus, such as in a beam dyer, a Pad-Roll, a Jigger/Winch, a J-Box, or Pad-Steam types of apparatus. The process preferably takes place during the finishing (post treatment) step.

In a preferred embodiment the process of the invention may be accomplished on cyclic oligomers of poly(ethylene terephthalate) present on and/or in fibers or in yarn or fabric made (or partially made) from poly(ethylene terephthalate) fibers. Thus, the polyester yarn or fabric may be any yarn or fabric that is made from pure poly(ethylene terephthalate), or that is made from blends of poly(ethylene terephthalate) fibers and any other material conventionally used for making yarns or fabrics.

Thus, in a preferred embodiment, the invention provides a process for enzymatic treatment of polyester fibers, which process comprises subjecting the polyester fiber or fabric to the action of one or more carboxylic ester hydrolases, in particular lipolytic and/or biopolyester hydrolytic enzyme(s).

The polyester fabric may be any fabric or fabric blend comprising polyester. Preferably the fabric comprises more than 50% (w/w) of polyester, in particular more than 75% (w/w) of polyester, more than 90% (w/w) of polyester, or more than 95% (w/w) of polyester. In a most preferred embodiment, the process of the invention is applied to fabrics or textiles or yarns consisting essentially of poly (ethylene terephthalate) polyester material, i.e. pure poly (ethylene terephthalate) polyester material.

Hydrolytic Enzymes

The enzymatic finishing process of the invention may be accomplished using any carboxylic ester hydrolases, in particular lipolytic enzyme and/or any biopolyester hydrolytic enzyme. Such enzymes are well known and defined in the literature, cf. e.g. Borgström B and Brockman H L, (Eds.); *Lipases*; Elsevier Science Publishers B.V., 1984, and Kolattukudy P E; *The Biochemistry of Plants*, Academic Press Inc., 1980 4 624–631.

In the context of this invention lipolytic enzymes include true lipases, esterases, phospholipases, and lyso-phospholipases. More specifically the lipolytic enzyme may be a lipase as classified by EC 3.1.1.3, EC 3.1.1.23 and/or EC 3.1.1.26, an esterase as classified by EC 3.1.1.1, EC 3.1.1.2, EC 3.1.1.6, EC 3.1.1.7, and/or EC 3.1.1.8, a phospholipase as classified by EC 3.1.1.4 and/or EC 3.1.1.32, and a lyso-phospholipase as classified by EC 3.1.1.5.

The lipolytic enzyme preferably is of microbial origin, in particular of bacterial, of fungal or of yeast origin.

In a particular embodiment, the lipolytic enzyme used may be derived from a strain of *Absidia*, in particular *Absidia blakesleena* and *Absidia corymbifera*, a strain of *Achromobacter*, in particular *Achromobacter iophagus*, a strain of *Aeromonas*, a strain of *Alternaria*, in particular *Alternaria brassiciola*, a strain of *Aspergillus*, in particular *Aspergillus niger* and *Aspergillus flavus*, a strain of *Achromobacter*, in particular *Achromobacter iophagus*, a strain of *Aureobasidium*, in particular *Aureobasidium pullulans*, a strain of *Bacillus*, in particular *Bacillus pumilus, Bacillus strearothermophilus* and *Bacillus subtilis*, a strain of *Beauveria*, a strain of *Brochothrix*, in particular *Brochothrix thermosohata*, a strain of *Candida*, in particular *Candida cylindracea* (*Candida rugosa*), *Candida paralipolytica*, and *Candida antarctica*, a strain of *Chromobacter*, in particular *Chromobacter viscosum*, a strain of *Coprinus*, in particular *Coprinus cinerius*, a strain of *Fusarium*, in particular *Fusarium oxysporum, Fusarium solani, Fusarium solani pisi,* and *Fusarium roseum culmorum*, a strain of *Geotricum*, in particular *Geotricum penicillatum*, a strain of *Hansenula*, in particular *Hansenula anomala*, a strain of *Humicola*, in particular *Humicola brevispora, Humicola brevis* var. *thermoidea*, and *Humicola insolens*, a strain of *Hyphozyma*, a strain of *Lactobacillus*, in particular *Lactobacillus curvatus*, a strain of *Metarhizium*, a strain of *Mucor*, a strain of *Paecilomyces*, a strain of *Penicillium*, in particular *Penicillium cyclopium, Penicillium crustosum* and *Penicillium expansum*, a strain of *Pseudomonas* in particular *Pseudomonas aeruginosa, Pseudomonas alcaligenes, Pseudomonas cepacia* (syn. *Burkholderia cepacia*), *Pseudomonas fluorescens, Pseudomonas fragi, Pseudomonas maltophilia, Pseudomonas mendocina, Pseudomonas mephitica lipolytica, Pseudomonas alcaligenes, Pseudomonas plantari, Pseudomonas pseudoalcaligenes, Pseudomonas putida, Pseudomonas stutzeri,* and *Pseudomonas wisconsinensis*, a strain of *Rhizoctonia*, in particular *Rhizoctonia solani*, a strain of *Rhizomucor*, in particular *Rhizomucor miehei*, a strain of Rhizopus, in particular *Rhizopus japonicus, Rhizopus microsporus* and *Rhizopus nodosus*, a strain of *Rhodosporidium*, in particular *Rhodosporidium toruloides*, a strain of *Rhodotorula*, in particular *Rhodotorula glutinis*, a strain of *Sporobolomyces*, in particular *Sporobolomyces shibatanus*, a strain of *Thermomyces*, in particular *Thermomyces lanuginosus* (formerly *Humicola lanuginosa*), a strain of *Thiarosporella*, in particular *Thiarosporella phaseolina*, a strain of *Trichoderma*, in particular *Trichoderma harzianum*, and *Trichoderma reesei*, and/or a strain of *Verticillium*.

In a more preferred embodiment, the lipolytic enzyme used according to the invention is derived from a strain of *Aspergillus*, a strain of *Achromobacter*, a strain of *Bacillus*, a strain of *Candida*, a strain of *Chromobacter*, a strain of *Fusarium*, a strain of *Humicola*, a strain of *Hyphozyma*, a strain of *Pseudomonas*, a strain of *Rhizomucor*, a strain of *Rhizopus*, or a strain of *Thermomyces*.

In a more preferred embodiment, the lipolytic enzyme used according to the invention is derived from a strain of *Bacillus pumilus*, a strain of *Bacillus stearothermophilus* a strain of *Candida cylindracea*, a strain of *Candida antarctica*, in particular *Candida antarctica* Lipase B (obtained as described in WO 88/02775), a strain of *Humicola insolens*, a strain of *Hyphozyma*, a strain of *Pseudomonas cepacia*, or a strain of *Thermomyces lanuginosus*.

In the context of this invention biopolyester hydrolytic enzyme include esterases and poly-hydroxyalkanoate depolymerases, in particular poly-3-hydroxyalkanoate depolymerases. In fact an esterase is a lipolytic enzyme as well as a biopolyester hydrolytic enzyme.

In a more preferred embodiment, the esterase is a cutinase or a suberinase. Also in the context of this invention, a cutinase is an enzyme capable of degrading cutin, cf. e.g. Lin T S & Kolaffukudy P E, *J. Bacteriol.* 1978 133 (2) 942–951, a suberinase is an enzyme capable of degrading suberin, cf. e.g., Kolattukudy P E; *Science* 1980 208 990–1000, Lin T S & Kolattukudy P E; *Physiol. Plant Pathol.* 1980 17 1–15, and *The Biochemistry of Plants*, Academic Press, 1980 Vol. 4 624–634, and a poly-3-hydroxyalkanoate depolymerase is an enzyme capable of degrading poly-3-hydroxyalkanoate, cf. e.g. Foster et al., *FEMS Microbiol. Lett.* 1994 118 279–282. Cutinases, for instance, differs from classical lipases in that no measurable activation around the critical micelle concentration (CMC) of the tributyrine substrate is observed. Also, cutinases are considered belonging to a class of serine esterases.

The biopolyester hydrolytic enzyme preferably is of microbial origin, in particular of bacterial, of fungal or of yeast origin.

In a preferred embodiment, the biopolyester hydrolytic enzyme is derived from a strain of *Aspergillus*, in particular *Aspergillus oryzae*, a strain of *Alternaria*, in particular *Alternaria brassiciola*, a strain of *Fusarium*, in particular *Fusarium solani, Fusarium solani pisi, Fusarium roseum culmorum*, or *Fusarium roseum sambucium*, a strain of *Helminthosporum*, in particular *Helminthosporum sativum*, a strain of *Humicola*, in particular *Humicola insolens*, a strain of *Pseudomonas*, in particular *Pseudomonas mendocina*, or *Pseudomonas putida*, a strain of *Rhizoctonia*, in particular *Rhizoctonia solani*, a strain of *Streptomyces*, in particular *Streptomyces scabies*, or a strain of *Ulocladium*, in particular *Ulocladium consortiale*. In a most preferred embodiment the biopolyester hydrolytic enzyme is a cutinase derived from a strain of *Humicola insolens*, in particular the strain *Humicola insolens* DSM 1800.

In another preferred embodiment, the poly-3-hydroxyalkanoate depolymerase is derived from a strain of *Alcaligenes*, in particular *Alcaligenes faecalis*, a strain of Bacillus, in particular *Bacillus megaterium*, a strain of *Comamonas*, in particular *Comamonas testoroni*, a strain of *Penicillium*, in particular *Penicillium funiculosum*, a strain of *Pseudomonas*, in particular *Pseudomonas fluorescens, Pseudomonas lemoignei* and *Pseudomonas oleovorans*, or a strain of *Rhodospirillum*, in particular *Thodospirillum rubrum*.

Process Conditions

The enzymatic treatment according to the present invention preferably is carried out as a wet process. It is at present contemplated that a suitable liquor:textile ratio may be in the range of from about 20:1 to about 1:1, preferentially in the range of from about 15:1 to about 5:1.

Enzyme dosage must be a function of the enzyme(s) applied and the reaction time and conditions given. It is at present contemplated that the enzyme(s) may be dosed in a total amount of from about 0.001 g/kg to about 5 g/kg enzyme per yarn or fabric, preferably from about 0.001 g/kg to about 0.5 g/kg.

The enzymatic hydrolysis may be carried out in the temperature range of from about 30° C. to about 100° C., preferentially from about 50° C. to about 100° C. The pH range may, dependent on the enzyme(s) applied, be from about pH 4 to pH 11. It is at present contemplated that a suitable reaction time may be in the range of from about 15 minutes to about 3 hours.

The process of the invention may further comprise the addition of one or more chemicals capable of improving the enzyme-substrate interaction (in order to improve the substrate's accessibility and/or dissolve reaction products), which chemicals may be added prior to, or simultaneously with the enzymatic treatment. Such chemicals may in particular be surfactants, wetting agents, and dispersing agents, or mixtures hereof.

The process of the invention may optionally comprise a rinsing step during which the hydrolyzed cyclic oligomers are subjected to rinsing, in particular to rinsing with dilute alkali. Dilute alkali dissolves linear fragments of the cyclic oligomers, and may to some extent further hydrolyze these linear fragments.

In the context of this invention dilute alkali comprise aqueous solutions having a pH in the range of from about pH 7 to about pH 11, more preferably of from about pH 7 to about pH 10, most preferred of from about pH 7 to about pH 9. A buffer may be added to the medium.

EXAMPLES

The invention is further illustrated in the following examples, which are not intended to be in any way limiting to the scope of the invention as claimed.

Example 1

In this example eleven different enzymes with lipolytic and/or biopolyester hydrolytic activity are examined for their activity towards cyclic oligomers of poly(ethylene terephthalate). The cyclic oligomers are obtained from polyester fabric by Soxhlet extraction with 1,4-dioxane.

The eleven enzymes tested in this example are:
*Bacillus pumilus* lipase (obtained as described in WO 91/16422);
*Bacillus stearothermophilus* lipase (obtained as described in JP 64/744992);
*Candida antarctica* Lipase B (obtained as described in WO 88/02775);
*Candida cylindracea* (=*Candida rugosa*) lipase (obtained from Nippon Oil & Fats Co. Ltd., Japan);
*Pseudomonas cepacia* lipase (obtained as described in EP 331,376);
Glucosaminated Lipolase™ (obtained as described in WO 95/09909);
*Thermomyces lanuginosus* (formerly *Humicola lanuginosa*) lipase (obtained as described in EP 305,216);
Recombinantly produced guinea pig lipase (rGPL) (obtained as described in WO 93/00426);
*Humicola insolens* cutinase (actually a lipase also having cutinase activity, obtained from the strain *Humicola insolens* DSM 1800 as described in Example 2 of U.S. Pat. No. 4,810,414);
*Aspergillus aculeatus* pectin methyl esterase (PME; obtained as described in WO 94/25575); and
*Aspergillus aculeatus* acetyl esterase (AE; obtained as described in WO 95/02689).

The substrate solution is incubated with the hydrolytic enzyme preparation in an agar gel containing phenol-red. 1000 ml agar gel is prepared from 17 g Agarose type 2 medium EEO (Sigma, A-6877), 3 g $NaNO_3$, 1 g $K_2HPO_4$, 0.5 g KCl, 1 ml 1% (w/v) $FeSO_4$, and 50 ml 0.4 g/l phenol-red solution, pH adjusted to 8.0–8.5.

TABLE 1

Clarification Zones

| Strain | Enzyme type | Activity on tributyrine | Activity on cyclic oligo. |
|---|---|---|---|
| Blank | | 0 | 0 |
| *Bacillus pumilus* lipase | Bacterial lipase | 3 | 1 |
| *Bacillus stearothermophilus* lipase | Bacterial lipase | 3–4 | 1 |
| *Candida antartica* Lipase B | Fungal lipase | 3 | 0–1 |
| *Candida cylindracea* (*rugosa*) lipase | Fungal lipase | 4 | 0–1 |
| *Pseudomonas cepacia* lipase | Fungal lipase | 5 | 1 |
| *Thermomyces lanuginosus* lipase | Fungal lipase | 4 | 1 |
| Glucosaminated Lipolase□ | Mod. Fungal lipase | 3 | 0–1 |
| Recombinant guinea pig lipase | Rec. Mammal lipase | 4 | 2 |
| *Humicola insolens* cutinase | Fungal cutin esterase | 4 | 1 |
| *Aspergillus aculeatus* PME | Fungal pectin methyl esterase | 0 | 0–1 |
| *Aspergillus aculeatus* AE | Fungal acetyl esterase | 0 | 1 |

The substrate solution, 15 Π tributyrine or cyclic oligomers, is poured into plug holes in the agar, and the aqueous enzyme solution is mixed into the substrate solution. If the enzyme is capable of hydrolyzing the substrate, then acids are formed and diffuse into the gel, where the pH indicator phenol-red turns from red to yellow.

Example 2

In this example a lipolytic and biopolyester hydrolytic enzyme (*Humicola insolens* cutinase derived from the strain *Humicola insolens* DSM 1800 as described in WO 96/13580) is examined for activity towards cyclic tri(ethylene terephthalate). The cyclic trimer is obtained from polyester fabric by Soxhlet extraction with 1,4-dioxane, and is further purified by ethanol and 1,4-dioxane washes.

A mixture of the following composition is incubated at 30° C. for 16 hours:
  0.25 ml glycylglycine buffer, 0.2 M pH 8.5
  2.50 ml de-ionized water
  0.25 ml cyclic trimer, 5.0 mM in 1,4-dioxane
  62.5 μg of enzyme The reaction is stopped by adding 5.0 ml 1,4-dioxane, and the mixture is analyzed on a reverse phase HPLC, ODS (octa dodecyl silicate) column eluted with acetonitrile and pH 3.0 phosphate-buffer. Detection of the reaction products is carried out spectrophotometrically at 240 nm, at which wavelength the terephthalic acid and terephthalate derivatives adsorb.

TABLE 2

Reaction Products as Determined by HPLC

| Peak Area, 240 nm | Blank | *Humicola insolens* cutinase |
|---|---|---|
| Cyclic trimer (17.6 min.) | 8.07 (100%) | 3.69 (44%) |
| Product 1 (3.8 min.) | 0.00 (0%) | Trace (<5%) |
| Product 2 (4.5 min.) | 0.00 (0%) | 2.26 (27%) |
| Product 3 (5.3 min.) | 0.00 (0%) | Trace (<5%) |
| Product 4 (13.0 min.) | 0.00 (0%) | 2.40 (29%) |
| Total area, 240 nm | 8.07 | 8.35 |

In this example 56% of the cyclic tri(ethylene terephthalate) is degraded under the given conditions by the cutinase from *Humicola insolens*, yielding four detectable degradation products.

Following this experiment three of these products have been identified as ethylene bis(terephthalic acid) ester (MW=342), terephthalic acid mono(2-hydroxyethyl) ester (MW=210) and terephthalic acid (MW=166).

The invention claimed is:

1. A process for enzymatic hydrolysis of cyclic oligomers of poly(ethylene terephthalate) present in or on a fabric or yarn containing poly(ethylene terephthalate) fibers, said process comprises subjecting the fabric or yarn to the action of one or more microbial carboxylic ester hydrolases.

2. The process according to claim 1, wherein said one or more microbial carboxylic ester hydrolases is a lipolytic or biopolyester hydrolytic enzyme.

3. The process according to claim 2, wherein the lipolytic enzyme is selected from the group consisting of a lipase, an esterase, a phospholipase, and a lyso-phospholipase.

4. The process according to claim 3, wherein the esterase is derived from a strain of *Aspergillus*, a strain of *Alternaria*, a strain of *Fusarium*, a strain of *Helminthosporum*, a strain of *Humicola*, a strain of *Pseudomonas*, a strain of *Rhizoctonia*, a strain of *Streptomyces*, or a strain of *Ulocladium*.

5. The process according to claim 3, wherein the esterase is a cutinase derived from a strain of *Humicola insolens*.

6. The process according to claim 2, wherein the biopolyester hydrolytic enzyme is selected from the group consisting of an esterase and a poly-hydroxyalkanoate depolymerase.

7. The process according to claim 6, wherein the esterase is selected from the group consisting of a cutinase and a suberinase.

8. The process according to claim 6, wherein the poly-hydroxyalkanoate depolymerase is derived from a strain of *Alcaligenes*, a strain of *Bacillus*, a strain of *Comamonas*, a strain of *Penicillium*, a strain of *Pseudomonas*, or a strain of *Rhodospirillum*.

9. The process according to claim 1, further comprising the addition of one or more chemicals for improving the enzyme-substrate interaction.

10. The process according to claim 9, wherein the one or more chemicals are selected from the group consisting of a surfactant, a wetting agent, and a dispersing agent.

11. The process according to claim 1, further comprising a rinsing step following the action of the one or more microbial carboxylic ester hydrolases.

12. The process according to claim 1, in which the cyclic oligomer is cyclic tri(ethylene terephthalate).

13. The process according to claim 2, wherein the lipolytic enzyme is a lipase derived from a strain of *Aspergillus*, a strain of *Achromobacter*, a strain of *Bacillus*, a strain of *Candida*, a strain of *Chromobacter*, a strain of *Fusarium*, a strain of *Humicola*, a strain of *Hyphozyma*, a strain of *Pseudomonas*, a strain of *Rhizomucor*, a strain of *Rhizopus*, or a strain of *Thermomyces*.

14. The process according to claim 2, wherein the lipolytic enzyme is a lipase derived from a strain of *Bacillus pumflus*, a strain of *Bacillus stearothermophilus* a strain of *Candida cylindracea*, a strain of *Candida antarctica*, a strain of *Humicola insolens*, a strain of *Hyphozyma*, a strain of *Pseudomonas cepacia*, or a strain of *Thermomyces lanuginosus*.

15. The process according to claim 2, wherein the lipolytic enzyme is a phospholipase or lyso-phospholipase derived from a strain of *Achromobacter*, a strain of *Candida*, or a strain of *Pseudomonas*.

16. The process of claim 1, wherein the process takes place during finishing.

17. The process of claim 1, wherein the process is carried out as a wet process.

18. The process of claim 1, wherein the process is carried out at a temperature in the range from about 30° C. to about 100° C.

* * * * *